United States Patent [19]

Tibbetts et al.

[11] Patent Number: 4,775,630

[45] Date of Patent: Oct. 4, 1988

[54] TRANSCRIPTIONAL CONTROL ELEMENT ADAPTED FOR REGULATION OF GENE EXPRESSION IN ANIMAL CELLS

[75] Inventors: Clark Tibbetts, Nashville, Tenn.; Pamela L. Larsen, Cambridge, Mass.; Stephen N. Jones, Nashville, Tenn.; Mary M. McGrane, Cleveland Heights, Ohio

[73] Assignee: Vanderbilt University, Nashville, Tenn.

[21] Appl. No.: 897,042

[22] Filed: Aug. 15, 1986

[51] Int. Cl.$^4$ ........................ C12P 21/00; C12P 19/00; C12N 15/00; C07H 15/12

[52] U.S. Cl. ...................................... 435/320; 435/68; 435/70; 435/91; 435/172.3; 435/235; 536/27; 935/27; 935/32; 935/34; 935/56

[58] Field of Search ................. 435/68, 70, 91, 172.1, 435/172.3, 253, 240, 320, 948, 235; 536/27; 935/27, 32, 34, 41, 43, 56, 70

[56] References Cited

PUBLICATIONS

Borrelli et al., Nature, vol. 312, 13 Dec. 1984, pp. 608–612, "Adenovirus-2 E1A Products Repress Enhancer Induced Stimulation of Transcription".

Larsen et al., (Including Christine Robinson), Virology, vol. 155, pp. 148–159, Nov. 1986, 3: Ad3hr15 "An E1A Mutant Type has Reiterated DNA Sequences 5' to its E1A Gene."

Hearing et al., Cell, vol. 33, pp. 695–703, Jul. 1983, "The Adenovirus Type 5 E1A Transcriptional Control Element Contains a Duplicated Enhancer Element".

Robinson et al., Virology, vol. 137, pp. 276–284, 1984, "Polar Encapsidation of Adenovirus DNA: Evolutionary Variants Reveal Dispensible Sequences Near the Left Ends of Ad3 Genomes."

Leite et al., Gene, vol. 41, Apr. 1986, pp. 207–215, "Expression of the Chloramphenicol Acetyl Transferase Gene in Human Cells . . . Other Subgroups on Gene Expression".

Kostruko et al., J. Virology, vol. 43(3), pp. 1132–1137, Sep. 1986, "Polardencapsidation of Adenovirus DNA: Cloning and DNA Sequence of the Left end of Ad type 3".

Hearing et al., Cell, vol. 45, pp. 229–236, Apr. 25, 1986, "The Adenovirus Type 5 E1A Enhancer Contains Two Functionally Distinct Domains: One is Specific . . . Units in Cis".

Kaufman, Proc. Natl. Acad. Sci., vol. 82, pp. 689–693, Feb. 1985, "Identification of the Components Necessary for Adenovirus Translational Control . . . Expression Vectors".

Larsen et al., Virology, vol. 147, pp. 187–200, Nov. 1985, "Spontaneous Reiterations of DNA Sequences Near the Ends of Adenovirus Type 3 Genomes".

Tibbetts et al., J. Virology, vol. 57(3), Mar. 1986, "Autoregulation of Adenovirus E1A Gene Expression".

Primary Examiner—Thomas G. Wiseman
Assistant Examiner—Robin L. Teskin
Attorney, Agent, or Firm—Tilton, Fallon, Lungmus & Chestnut

[57] ABSTRACT

A novel alteration of a viral DNA sequence, derived from a human adenovirus type 3 mutant (Ad3) designaed Ad3h15, provides a transcriptional control element which can be used to regulate expression of a selected gene in animal and human cells. The Ad3h15 control element blocks transcription of a controlled gene in the presence of the products of the Ad3 E1A gene, and amplifies transcription in the presence of type 5 (Ad5) adenovirus E1A gene products.

4 Claims, 1 Drawing Sheet

U.S. Patent  Oct. 4, 1988  4,775,630 pAd3h15 PLASMID
(3030 bp)

TRANSCRIPTIONAL CONTROL ELEMENT ADAPTED FOR REGULATION OF GENE EXPRESSION IN ANIMAL CELLS

GRANT REFERENCE

This invention was developed in part under PHS Grant CA34126, National Cancer Institute, Department of Health and Human Services.

FIELD OF INVENTION, BACKGROUND, AND PRIOR ART

The field of the invention is recombinant DNA technology. The invention is particularly concerned with a genetic control element derived from an adenovirus.

The control region of the adenovirus genome and its relation to the E1A gene has been extensively studied. It is known that the protein products of the adenovirus E1A gene may act as positive and negative regulators of early viral gene expression, and that E1A products regulate at the transcriptional level. Sequences located 5' to the early viral regions contain sites which confer regulation by the E1A gene product. Weeks and Jones, *Mol. Cell. Biol.* (1983), 3:1222–1234. Positive and negative autoregulation of the adenovirus E1A gene transcription has been reported. Tibbetts et al., *J. Virol.* (1986) 57:1055–1064.

The E1A control region and E1A gene for adenovirus type 3 (Ad3) have been incorporated in plasmid vectors; the Ad3 control region and Ad3 E1A gene have been sequenced. Kosturko, et al., *J. Virol.* (1982), 43:1132–1137. Variant genomes of the Ad3 control region have been produced by repeated passage of the adenovirus in HeLa cells. Robinson and Tibbetts, *Virology* (1984), 137:276–286. The reported variations occurred in the left-most 750 bp of the genome. However, the mutants retained the first 135 bp, comprising the inverted terminal repeat region (ITR) of the Ad3 strain. In particular, the variations occurred in the 440 bp between the ITR and the initiation codon (AUG) at bp 575.

The sequences between ITR and AUG have been shown to include enhancer sequences for adenovirus type 5. Hearing and Shenk, *Cell* (1983), 33:695. The two enhancer fragments found by these authors were composed of different nucleotide sequences, and were separated from each other by intervening DNA.

SUMMARY OF INVENTION

A variant of an adenovirus type 3 (Ad3) control region has been discovered which includes a gene expression regulator sequence followed in tandem by a duplicate thereof. The tandem regulator of this variant is especially sensitive to repression by the products of the Ad3 E1A gene under its control. However, when Ad5 E1A products are provided, or in the absence of Ad3 E1A products, a controlled gene can be expressed, and the expression amplified by Ad5 E1A products. Initial repression of tandem regulator can be overcome by the later presence of Ad5 E1A products.

The Ad3 control region variant can be used without the Ad3 E1A gene present for constitutive expression of the controlled gene. Thus, various protocols and E1A products can be selected to repress or amplify expression of a gene under control of the tandem promoter. This control region can be used as a regulator of gene expression by plasmids which can be propagated in either prokaryotic or eukaryotic cells.

The gene of interest can be placed under control of the regulator for propagation of the cells to increase cell number under conditions (the presence of Ad3 E1A products) where the transcriptional control element restricts gene expression. When sufficient cells have been produced, transcription of the gene of interest can be induced by introduction of Ad5 E1A products. This can lead to high yields of the gene product.

The novel transcriptional control element of this invention can also be employed for other purposes. Rapid diagnostic assay of viruses having E1A genes or E1A-like genes may be achieved using cells transformed by and bearing a plasmid containing the novel E1A inducible control element linked to a probe gene. Analysis of the probe gene's product can be performed in parallel assays, infecting the cells with inocula treated or not treated with selected immune reagents.

It is believed that the transcriptional control element of this invention will find its most important application for the production of proteins in animal cells. Repressor/inducer-type regulators have been described for bacterial cells, but heretofore none have been known for use in animal cells. Such genetic engineering procedures may be essential for production of certain animal proteins.

THE DRAWING

FIG. 1 of the accompanying drawing is a representation of a plasmid, designated as pAd3h15, which is a hybrid plasmid formed from the pBR322 plasmid and the adenovirus DNA control sequences of this invention. This drawing will be subsequently further described.

DETAILED DESCRIPTION

Figure 1:
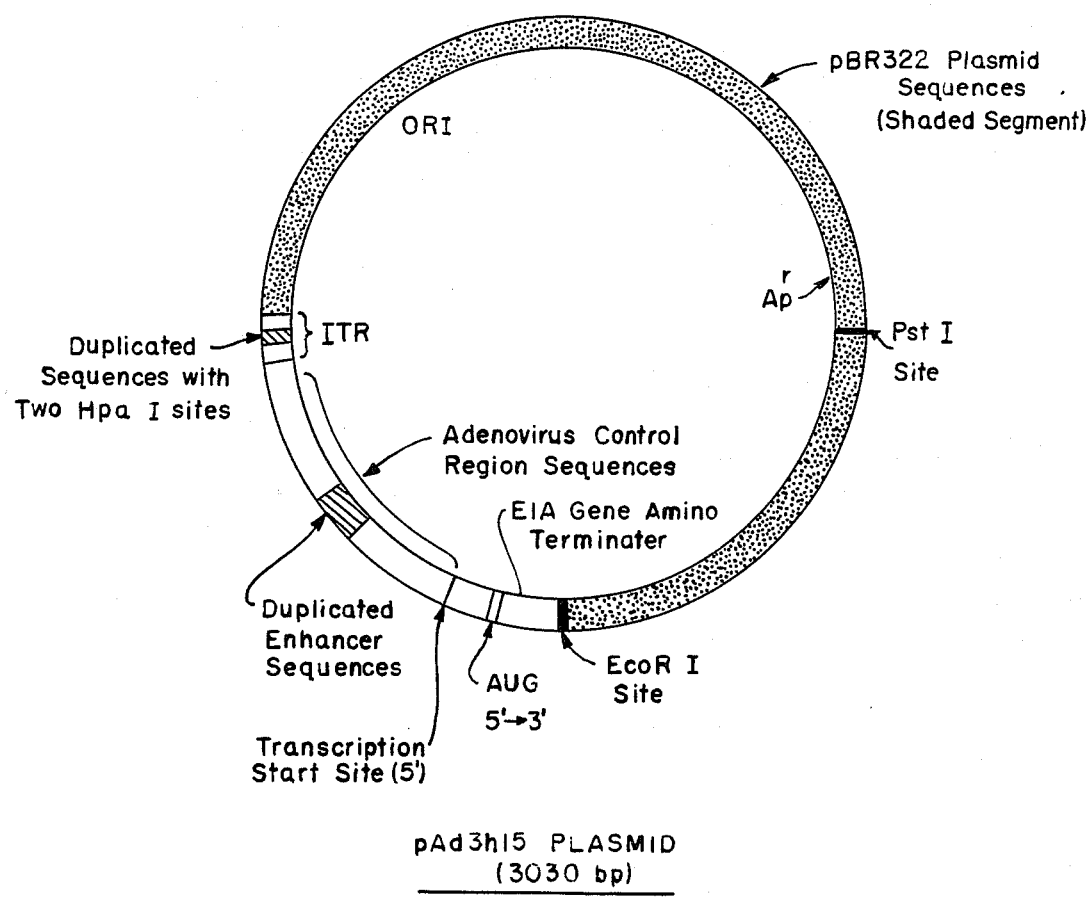

The control element of this invention was derived from a novel mutant of human adenovirus type 3 designated mutant Ad3h15. This mutant was found to be defective in the regulation of the transcription of its essential E1A gene. The segment of Ad3 viral DNA which lies 5' to the E1A gene normally comprises the 510 base pairs which are at the left end of the conventional Ad3 genome map. The sequence in this region of Ad3 DNA was determined by Kosturko et al., *J. Virol.* (1982), 43:1132–1137. An additional deoxycytidine residue was subsequently observed in the sequence at position bp 340, accounting for the BstNI cleavage site at this position (CCNGG). The segment of the mutant which is associated with the defective transcription regulation is 90 base pairs longer than the wild type Ad3 DNA segment. This elongation is due to two local tandem repetitions of viral DNA sequences. There are copies of the sequences in the wild-type Ad3 of from 69 to 98 bp and 281 to 340 bp, appearing, respectively, between nucleotides 98 and 99 and nucleotides 340 and 341.

The hybrid plasmid pAd3h15 was prepared from sequences of the now generally available vector pBR322, Bolivar et al., *Gene.* (1977), 4:121, and the sequences associated with the left end of the human adenovirus type 3 mutant Ad3h15. The pBR322 sequences (shaded segment in FIG. 1) correspond to the nucleotides from 2065 (former Pvu II restriction site) through the origin of plasmid DNA replication (ORI), the β-lactamase gene which confers ampicillin resistance ($Ap^r$) in host bacteria, and the Pst I restriction site to the plasmid EcoRI restriction site at nucleotide 4362/1. The left plasmid:viral junction joins the -CAG moiety of the pBR322's PvuII site to nucleotide 13 of the Ad3 mutant. (The mutant segment in FIG. 1 is shown unshaded with portions cross-hatched.) The junction was described for plasmid pCT132 by Kosturko et al. (1982), cited above.

The viral sequences of the mutant adenovirus E1A control region in the hybrid plasmid proceed from left to right through the inverted terminal repeat sequence (ITR, base pairs 14 to 165 of Ad3h15) through the viral sequences 5' to the E1A gene. The 5'-end of the viral E1A gene transcripts (from nucleotide 601 in Ad3h15) and the initiation codon (AUG, 665–667 for Ad3h15) are indicated in FIG. 1. For comparison with nucleotide sequences of other human adenoviruses, see van Ormondt et al., Gene (1980), 12:63. The viral sequences proceed through nucleotide 746 of Ad3h15 and are there joined to the pBR322 EcoRI site via an oligonucleotide linker which places an intervening deoxyguanosine nucleotide at the junction. Only the left-hand portion of the E1A gene is included as designated in FIG. 1, the E1A gene's amino-terminal portion.

The cross-hatched intervals in FIG. 1 correspond to the tandem repeat sequences associated with the altered control region DNA of the mutant Ad3h15. Comparison with the wild type Ad3 E1A transcriptional control element can be made by reference to Kosturko, et al. (1982), with the added dC residue at bp 340 as cited above. The duplicated sequences in the ITR region include two HpaI restriction sites, separated by 30 bp as indicated.

The plasmid represented in FIG. 1 has been permanently deposited with the American Type Culture Collection, 12301 Parklawn Drive, Rockville, Md. 20852. This plasmid (pAd3h15) has been assigned ATCC Accession No. 53156. In general, any plasmids can be employed as carriers of the Ad3h15 control region which plasmids are adapted for use as cloning or transcription vehicles.

The inclusion of the EcoRI site in the Ad3h15 plasmid is convenient for introduction of a gene of interest to be expressed under control of the pAd3h15 element The following protocol is illustrative. After cleavage of pAd3h15 by EcoRI, processive exonucleolytic digestion by BAL31 will remove nucleotides encoding up to the 26 amino acids of the amino-termini of Ad3E1A gene products, and thus place the amino terminus of the gene in the desired alignment with the 5'-noncoding sequences of the Ad3E1A gene. Alternatively, the gene may be cloned into the EcoRI site directly, postponing an alignment step for subsequent site-directed mutagenesis using synthetic oligonucleotides.

The pAd3h15 gene conjugate plasmid may be introduced into animal cells using conventional methods to obtain transient or permanent association with the cells. The Ad3h15 element will block transcription of the gene. Concomitant expression of adenovirus E1A or other E1A-like genes can lead to repression or activation of this transcription. The introduction of E1A activity can be achieved by conventional methods such as adenovirus (or other virus) infection of the animal cells. Alternatively the cells can be induced to fuse with 293 cells (which constitutively express the adenovirus type 5 E1A gene). In a further alternative, the cells can be transfected with plasmids capable of expressing adenovirus E1A (or other viral E1A-like) gene. The E1A genes selected may represent the wild-type or specifically altered sequences such as the cDNA equivalents.

Purified functional adenovirus E1A gene products have been isolated from bacteria expressing cDNA clones. See Ferguson et al. Science (1984), 224:1343. Such protein preparations of wild-type or derivative E1A proteins could be introduced directly into pAd3h15 gene transformed cells by liposome fusion method to repress or induce expression of the gene from its E1A-dependent Ad3h15 transcription element.

Thus the properties of the Ad3h15 transcriptional control element are remarkably suited to applications where it may be desirable to produce large quantities of a particular gene product in selected animal cells, as opposed to in bacterial or yeast cell cultures. This may be the case for proteins which require cell-specific post-transcriptional, or post-translational modifications or which present unique secretory or compartmentalization obstacles to production in bacteria or yeast cells The Ad3h15 element may be introduced into any of the known plasmid vectors for cloning or expression purposes.

As another application of the Ad3h15 transcriptional control element, if a gene (probe) having a readily assayed product is latent under Ad3h15 control in a transformed cell line, then exposure to viruses expressing E1A or E1A-like genes could induce the probe gene and provide the basis of a rapid viral diagnosis.

EXPERIMENTAL RESULTS

A prototype strain (G.B.) of human adenovirus type 3 (PAR for parental) was obtained from the American Type Culture Collection. A stock (HMP) of this virus after prolonged passage at high multiplicity had become heterogeneous in DNA sequences at the right and left ends of the viral genome. See Robinson and Tibbetts, Virology (1984), 137:276–286; Larsen and Tibbetts, Virology (1985), 147:187–200. Defective variants were isolated from this stock which showed selective growth of 293 cells as opposed to normally permissive HeLa or A549 cells. The 293 cells express the human adenovirus type 5 E1 genes. Spector et al., J. Virol. (1980) 35:860. The 293 cells therefore permit growth of adenovirus type 3 variants having defective E1 genes expression.

The selected variant, designated Ad3h15, was further studied. Table I sets forth the results of plaque assays of wild type adenovirus type 3 (strain G.B., PAR stock) and mutant Ad3h15 in two cell lines.

TABLE I

| Virus Stock | Particles/ml[a] | Pfu/ml[b] | Particles/Pfu |
|---|---|---|---|
| Ad3 PAR | $4.0 \times 10^{12}$ | $3.5 \times 10^{11}$ (A549) | 11 (A549) |
| | | $4.0 \times 10^{9}$ (293) | 1000 (293) |
| Ad3h15 | $2.4 \times 10^{12}$ | $1.5 \times 10^{5}$ (A549) | $1.6 \times 10^{7}$ (A549) |
| | | $6.5 \times 10^{9}$ (293) | 370 (293) |

[a]Ad3 PAR propagated on HeLa cells, Ad3h15 propagated in 293 cells. Virus purification and estimation of particles/ml described in Robinson and Tibbetts (1984) or references cited therein.
[b]Serial 10-fold dilutions of purified virions plated in duplicate or triplicate onto cultures of A549 cells. (Human lung carcinoma permissive for Ad3, like HeLa) or 293 cells (Ad5 DNA-transformed human embryonic kidney cell line); overlayed with agar, and incubated 15–20 days to observe plaque formation.

The results shown in Table I demonstrate that Ad3h15 virus grown in A549 cells is at least six others of magnitude less than wild type Ad3. In 293 cells Ad3h15 grows about three-fold better than wild type Ad3 on the basis of infectivity expressed as particles/plaque forming unit (PFU).

Selective Repression and Amplification

RNA was isolated at different times after infection of the Ad5 E1A-expressing 293 cells, and the normally permissive A549 cells by the wild-type Ad3 PAR or Ad3h15 mutant viruses. The RNA was electrophoresed through agarose-formaldehyde gels, transferred to "Genescreen," and probed with radiolabeled DNA representing E1A sequences of Ad3 PAR. Early after infection (3 to 6 hours) of A549 cells by the wild-type virus Ad3 E1A expression appeared as 12S and 13S mRNA with a smaller, 7S, species appearing late after infection. Ad3h15 shows remarkable variance from this typical pattern of adenovirus E1A gene expression. No evidence of E1A gene transcription was seen with the Ad3h15 virus in A549 cells. In 293 cells, however, intense transcription of the mutant's E1A gene is seen following an initial delay of about six hours after the infection. The early autoregulation repression by the Ad3 E1A gene products was overcome by the Ad5 E1A gene products expressed in the 293 cells. This was confirmed by another experiment in which the Ad3h15 promotor was transcribed in A549 cells also infected with Ad5 vuris, thereby providing Ad5 E1A gene products to release the block.

Summarizing, for the mutant Ad3h15 virus there are two novel results: (1) No detectable amounts of E1A gene products are produced by transcription of its E1A gene in the normally permissive A549 cells. (2) In 293 cells the Ad3h15 virus expresses its E1A gene at levels surpassing those of the wild type Ad3 virus in A549 cells. The conclusion follows tha Ad3h15 has altered regulation of its E1A gene such that early after infection of A549 cells there is substantially a transcriptional block (negative control). In the presence of Ad5E1A gene products (the Ad5 E1A of 293 cells) the transcription block is released, and Ad3h15's E1A gene is induced to very high levels. When A549 cells are coinfected with Ad3h15 virus and Ad5 virus, the Ad3h15 promotion functions after an initial repression delay and amplifies the gene expression. The conclusion to be drawn from these and other related experiments is that the Ad3h15 E1A promoter is unusually sensitive to autorepression by the Ad3 E1A products but that this repression can be overcome and expression amplified by introduction of Ad5 E1A products.

Marker Rescue Experiments

Marker rescue experiments were performed which were attempts to restore the capacity of Ad3h15 to form wild type plaques and grow in A549 cells. Either 293 or A549 cells were infected with Ad3h15 virus and transfected with plasmids containing different restriction fragments from the left end of Ad3 PAR. Recombination in vivo between the wild type sequences of the plasmid and the mutant sequences of Ad3h15 viral DNA would produce a virus genome with wild type phenotype.

In A549 cells, it was found that levels of marker rescue varied and were dependent upon capacity of the plasmid to express functional E1A gene products. When the infection/transfection was first performed on 293 cells (permissive for Ad3h15) followed by plaquing on A549 cells, smaller, non-E1A coding fragments were found capable of recombination rescue of the Ad3h15 defect. These results are summarized in Table II.

TABLE II

Marker Rescue of Ad3h15 in 293 Cells

Plates containing $10^7$ 293 cells were infected with Ad3h15 (MOI = $10^{-3}$) and subsequently transfected with plasmids bearing left-end, wild type Ad3 restriction fragments. Lysates of the infected/transfected 293 cells were diluted by $10^{-3}$ and 0.2 ml plated on A549 cells (6 × $10^6$ cells/plate) for plaque assay.

| Fragment | Plaques (duplicates) |
|---|---|
| Ad3h15 Alone | 0/0 |
| SalI-C, 6500 bp | 75/97 |
| SmaI-D, 3740 bp | 38/36 |
| Hind III-I, 1380 bp | 86/106 |
| BamHI-I, 750 bp | —/6 |
| PvuII-, 465 bp | 15/12 |

Since marker rescue was obtained with plasmids containing at least the left PvuII restriction fragment of Ad3 DNA, it was concluded that the lesion(s) responsible for the regulatory defects of Ad3h15 lies within the non-coding region upstream from the Ad3h15 gene. The mutant's E1A gene itself appeared normal and functional.

Plasmid Introduction and Cloning

The left end PvuII fragment of Ad3 is 465 bp. The sequence of mutant Ad3h15 DNA in this corresponding region was determined by the Maxam-Gilbert method. Intact viral DNA was end-labeled using Klenow fragment of DNA polymerase and radioactivity deoxynucleotides, followed by restriction and separation of the left and right end fragments for sequencing. The left end Ad3h15 Hind III-I fragment was cloned into a plasmid similar to that shown in FIG. 1, effectively substituting the sequences from the left end proximal viral Hpa I and Hind III sites with the sequences from Ad3h15 DNA.

Sequencing Analysis

The results of sequencing analysis are represented by the following diagram, which shows the complete sequences for the Ad3 viral portion of the pAd3h15 plasmid. A double stranded DNA of the adenovirus control region as found in the pAd3h15 plasmid is represented as the right-hand DNA strand. The letters A, T, G, and C have the standard meanings of adenine, thymine, guanine, and cystosine.

DIAGRAM A (1) ATACCTT AAGATGGAAT GGTGCCAACA TGTAAATGAG (37)

(38)                          (56)                                              (83)

GTAATTTAAA AAAGTGCGCG CTGTGTGGTG ATTGGCTGCG GGGTT AAC (85)

30 bp

-continued
DIAGRAM A

```
                                    Hpa I

(86)  CG  CTGTGTGGTG  ATTGGCTGCG  GGGTT AAC  (115)
              30 bp
                                    Hpa I (116) GG  CTAAAAGGGG  CGGCGCGACC  GTGGGAAAAT  GACGTGACTT  ATGTGGGAGG  (167)
(168) AGTTATGTTG  CAAGTTATTA  CGGTAAATGT  GACGTAAAAC  GAGGTGTGGT  (217)
(218) TTGAACACGG  AAGTAGACAG  TTTTCCCACG  CTTACTGACA  GGATATGAGG  (267)

(268)                                    (298)
                                           |
      TAGTTTTGGG  CGGATGCAAG  TGAAAATTCT  CCATTTTCGC  GCGAAAACTA  (307)

(308) AATGAGGAAG  TGAATTTCTG  AGTCATTTCG  CGGTTATGCC  (347)
                         60 bp (348)  CCATTTTCGC  GCGAAAACTA  (367)

(368)                                                (406)
                                                      |
      AATGAGGAAG  TGAATTTCTG  AGTCATTTCG  CGGTTATGCC  AGGGTGGAGT  (417)
                         60 bp (418) ATTTGCCGAG  GGCCGAGTAG  ACTTTGACCG  TTTACGTGGA  GGTTTCGATT  (467)
(468) ACCGTGTTTT  TCACCTAAAT  TTCCGCGTAC  GGTGTCAAAG  TCCTGTGTTT  (517)
(518) TTACGTAGGT  GTCAGCTGAT  CGTCAGGGTA  TTTAAACCTG  ACGAGTTCCG  (567)
(568) CTAAGAGGCC  ACTCTTGAGT  GCCAGCGAGA  AGAGTTTTCT  CCTCCGCGCC  (617)

(618)                          (643)
                                 |
      GCAAGTCAGT  TCTGCGCTTT  GAAATGAGA  CACCTGCGCT  TCCTGCCACA  (667)

(668) GGAGGTTATC  TCCAGTGAGA  CCGGGATCGA  AATACTGGAG  TTTGTGGTAA  (717)
(718) ATACC  (722)
```

As shown in Diagram A, two tandem repetitions of 60 bp (nucleotides 298–347 and 348–406; double underscoring) are found near the left end of Ad3h15 DNA. This is the region shown by marker rescue to alter the regulation of the E1A gene. The 30 bp duplications (nucleotides 56–85 and 86–115; single underscoring) are in the inverted terminal repeat region (ITR), and are therefore probably not required for the Ad3h15 phenotype regulation. The larger tandem repeats of 60 bp together are believed to be the sequences responsible for the Ad3h15 altered regulation. It was surprising that an enhancer region duplication should lead to a block of transcription (in the absence of E1A protein). Moreover, E1A products have recently been reported to repress transcription from enhancer-associated promoters: Borrelli et al., Nature (1984), 312:608; Velcich and Ziff, Cell (1985), 40:705. Thus it was also surprising that the 60 bp duplications in Ad3h15 result in greater E1A-induced levels of E1A transcription than found for wild type Ad3.

Shorter fragments containing the 60 bp tandem enhancer sequences can be prepared from the Ad3h15 plasmid. Again referring to Diagram A, it will be noted that the 30 bp duplicates (single underscoring) include Hpa I restriction sites. As indicated by the dotted lines the Hpa I endonuclease will cleave the sequence GTTAAC leaving blunt ends.

Referring to FIG. 1, it will be noted that the right-hand end of the Ad3 fragment (nucleotide 722) adjoins an EcoRI restriction site. The plasmid may therefore be treated with both Hpa I and EcoRI to produce a mixture of fragments. One fragment will extend from nucelotide 83 to 722, and the other from nucleotide 113 to 722. The Hpa I enzyme may be used at a low concentration to obtain cleavage at one or the other of the Hpa I sites rather than at both sites. The two fragments may be separated and recovered by gel electrophoresis and elution from gel fragments. Typical procedures for partial restriction digest and electrophoretic purification of DNA fragments are presented in Maniatis et al. (1982), "Molecular Cloning: A Laboratory Manual," Cold Spring Harbor Laboratory, New York.

Prior to Hpa I partial restriction the EcoRI restricted, linear plasmid DNA may be treated with endonuclease BAL31 under conditions selected to remove about 80 bp from each end of the DNA. Such conditions can be arranged following the procedures described in Maniatis et al. (1982) cited above. Subsequent ligations with the shortened, HpaI restricted fragment would be performed with the large HpaI to EcoRI fragment from non-BAL31 treated plasmid DNA. Alternatively a synthetic oligodeoxynucleotide could be prepared, having, in part, sequences upstream from and including the ATG start codon of the Ad3E1A proteins. The remaining sequence would be determined by the particular gene to be placed under control of the Ad3h15 regulator sequence. Site directed mutagenesis would be performed using the oligonucleotide as a template with the specific deletion of sequences required to provide promoter-gene alignment.

The smaller of the shortened fragments produced as described above is represented in the following Diagram B. The resulting fragment extends from nucleotide 113 through nucleotide 644. The duplicated enhancer sequences are indicated by double underscoring. The diagram is otherwise the same as that presented above for the complete Ad3 fragment in pAd3h15. The separated and shortened fragment may be employed as an expression regulator controlled by E1A product.

A plasmid containing the DNA sequences encoding a gene of interest (for example, a cDNA clone) would be restricted to provide an insertion site near the 5'-end of the cDNA sequences to be transcribed or near the AGT start codon of the gene. The DNA fragment containing the pAd3h15 control element would be cloned and plasmids then selected which provide the proper orientation of the mutant Ad3 viral promoter and the gene. Adjustments of promoter-gene alignment would be achieved through site-directed mutagenesis of selected plasmids.

2. The plasmid pAd3h15 (ATCC Accession No. 53156).

3. DNA fragments comprising the fragments obtained by cleaving plasmid pAd3h15 (ATCC Accession No. 53156) with the endonucleases EcoRI and HpA I.

4. A double stranded DNA fragment including the sequence represented by:
AACGG CTAAAAGGGG CGGCGCGACC GTGGGAAAAT GACGTGACTT ATGTGGGAGG AGTTATGTTG CAAGTTATTA CGGTAAATGT GACGTAAAAC GAGGTGTGGT TTGAACACGG AAGTAGACAG TTTTCCCACG CTTACTGACA

DIAGRAM B (118)                                       (113) AACGG
       CTAAAAGGGG CGGCGCGACC GTGGGAAAAT GACGTGACTT ATGTGGGAGG (168) AGTTATGTTG CAAGTTATTA CGGTAAATGT GACGTAAAAC GAGGTGTGGT
(218) TTGAACACGG AAGTAGACAG TTTTCCCACG CTTACTGACA GGATATGAGG (268) TAGTTTTGGG CGGATGCAAG TGAAAATTCT CCATTTTCGC GCGAAAACTA (308) AATGAGGAAG TGAATTTCTG AGTCATTTCG CGGTTATGCC (347)

(368)                                        (347) CCATTTTCGC GCGAAAACTA
                                             (406)
                                              |
      AATGAGGAAG TGAATTTCTG AGTCATTTCG CGGTTATGCC AGGGTGGAGT (418) ATTTGCCGAG GGCCGAGTAG ACTTTGACCG TTTACGTGGA GGTTTCGATT
(468) ACCGTGTTTT TCACCTAAAT TTCCGCGTAC GGTGTCAAAG TCCTGTGTTT
(518) TTACGTAGGT GTCAGCTGAT CGTCAGGGTA TTTAAACCTG ACGAGTTCCG
(568) CTAAGAGGCC ACTCTTGAGT GCCAGCGAGA AGAGTTTTCT CCTCCGCGCC
(618) GCAAGTCAGT TCTGCGCTTT GAAAATG (643)

We claim:

1. A hybrid DNA plasmid including a functional adenovirus transcriptional regulator region containing DNA sequences controlling expression of an adenovirus E1A gene, said controlling sequences including a transcriptional regulator sequence followed in tandem by a duplicate thereof, said regulator sequence responding to Ad3 E1A products to block the expression of a gene under its control and responding to Ad5 E1A gene products to unblock and amplify expression of the controlled gene, said tandem sequence consisting of double stranded DNA represented by CCATTTTCGC GCGAAAACTA AATGAGGAAG TGAATTTCTG AGTCATTTCG CGGTTATGCC, wherein A, T, G, and C respectively represent adenine, thymine, guanine and cystosine.

2. The plasmid pAd3h15 (ATCC Accession No. 53156).

3. DNA fragments comprising the fragments obtained by cleaving plasmid pAd3h15 (ATCC Accession No. 53156) with the endonucleases EcoRI and HpA I.

4. A double stranded DNA fragment including the sequence represented by:
AACGG CTAAAAGGGG CGGCGCGACC GTGGGAAAAT GACGTGACTT ATGTGGGAGG AGTTATGTTG CAAGTTATTA CGGTAAATGT GACGTAAAAC GAGGTGTGGT TTGAACACGG AAGTAGACAG TTTTCCCACG CTTACTGACA GGATATGAGG TAGTTTTGGG CGGATGCAAG TGAAAATTCT CCATTTTCGC GCGAAAACTA AATGAGGAAG TGAATTTCTG AGTCATTTCG CGGTTATGCC CCATTTTCGC GCGAAAACTA AATGAGGAAG TGAATTTCTG AGTCATTTCG CGGTTATGCC AGGGTGGAGT ATTTGCCGAG GGCCGAGTAG ACTTTGACCG TTTACGTGGA GGTTTCGATT ACCGTGTTTT TCACCTAAAT TTCCGCGTAC GGTGTCAAAG TCCTGTGTTT TTACGTAGGT GTCAGCTGAT CGTCAGGGTA TTTAAACCTG ACGAGTTCCG CTAAGAGGCC
wherein A, T, G, and C respectively represent adenine, thymine, guanine and cystosine.

* * * * *